(12) United States Patent
Kuno et al.

(10) Patent No.: US 6,761,173 B1
(45) Date of Patent: Jul. 13, 2004

(54) EAR PLUG TO BE INSERTED INTO THE EXTERNAL AUDITORY CANAL

(75) Inventors: Takashi Kuno, Akiruno (JP); Kenjiro Owada, Tokyo (JP); Masahiko Ohgushi, Tachikawa (JP)

(73) Assignee: Mimy Electronics Co., Ltd., Tokyo (JP)

( * ) Notice: Subject to any disclaimer, the term of this patent is extended or adjusted under 35 U.S.C. 154(b) by 0 days.

(21) Appl. No.: 10/337,362

(22) Filed: Jan. 7, 2003

(51) Int. Cl.[7] .............................................. A61F 11/00
(52) U.S. Cl. ...................................... 128/864; 128/865
(58) Field of Search ................................ 128/864–868

(56) References Cited

U.S. PATENT DOCUMENTS 3,783,864 A * 1/1974 Moller ........................ 128/152
3,872,559 A * 3/1975 Leight ........................ 128/151

* cited by examiner

Primary Examiner—Michael A. Brown
(74) Attorney, Agent, or Firm—Armstrong, Kratz, Quintos, Hanson & Brooks, LLP

(57) ABSTRACT

An ear plug to be inserted into the external auditory canal, having a compressible sleeve member and a core member attached therein, the improvement in which plural projections or a single projection are formed intermittently or continuously on an exterior of the core member, and vent is formed through or along the projection to make the external auditory canal communicate with the external atmosphere when inserted into the external auditory canal. A communicating passage or vent to an effective degree for remarkably decreasing the pressure difference between the inside of the external auditory canal and the external atmosphere as well as preventing leakage of sound causing so-called howling.

14 Claims, 2 Drawing Sheets

EAR PLUG TO BE INSERTED INTO THE EXTERNAL AUDITORY CANAL

INDUSTRIAL FIELD OF THE INVENTION

The present invention relates to an ear plug usable for prevention of noise, acoustic instruments such as hearing aids, and so on.

PRIOR ART

FIG. 1 shows the prior art ear plug wherein a sponge-like sleeve member 2 is fixed on an exterior of a core member 1 in a body. An external enlarged portion 1a of the core member 1 has a shallow vent 3 formed therethrough to loose a pressure difference between an interior of the external auditory canal and the external atmosphere when the ear plug is inserted into the external auditory canal. The core member 1 is formed as a part of a hearing aid 12.

It is required that the ear plug is superior in prevention of noise of high frequency when inserted into the external auditory canal. However, if the degree of prevention of noise is improved at that time, there occurs a pressure difference between the external atmosphere and an inside of the external auditory canal, accompanied by problems such as feeling of oppression with clogging of the ear. The pressure difference can be avoided by manufacturing the core member 1 in a straight form, however, sound generated from the hearing aid 12 having an external portion 1a of the core member 1 is easy to leak outward due to the short length of the vent in the core member 1. This causes so-called howling to remarkably decrease the performance of the ear plug.

OBJECT OF THE INVENTION

Consequently, an object of the present invention is to lengthen a communicating passage or vent to an effective degree for remarkably decreasing the pressure difference between the inside of the external auditory canal and the external atmosphere as well as preventing leakage of sound causing so-called howling.

CONSTITUTION OF THE INVENTION

In order to realize this object, the present invention provides an ear plug to be interted into the external auditory canal, having a compressible sleeve member and a core member attached therein, the improvement in which plural projections or a single projection are formed intermittently or continuously on an exterior of the core member, and vent is formed through or along the projection to make the external auditory canal communicate with the external atmosphere when inserted into the external auditory canal.

According to the present invention, the projections are formed on the exterior of the core member and the vent is defined through or along the projection to make the external auditory canal communicate with the external atmosphere, so as to lengthen a communicating passage or vent to an effective degree for remarkably decreasing only the pressure difference between an inside of the external auditory canal and the external atmosphere as well as preventing leakage of sound causing so-called howling.

In the present invention, it is preferable that an innermost vent is formed through an innermost projection of the intermittently formed projections or through an inner end portion of the core member to open into the external auditory canal, other vents are formed through other respective projections, and an outermost vent is formed through an outer end portion of the core member to open into the external atmosphere.

In this case, the vents are preferably formed at different positions of adjacent projections, and each of the projections can be ring-shaped.

It is also preferable that a continuous vent or groove is formed along the continuously formed projection to make an outermost vent communicate with the external auditory canal, and an outermost vent is formed through an outer end portion of the core member to open into the external atmosphere.

In this case, an additional vent is preferably formed through an inner end potion of the core member, and the continuously formed projection can be spiral-shaped.

It is further preferable that the sleeve member is composed of a sponge-like material such as polyurethane and the core member is composed of a flexible material such as polyethylene, so as to be deformed to meet the shape of the external auditory canal, and that a penetrating lumen is formed through an inside of the core member from one end to another end.

A hearing aid can has the core member in one body.

Figure 1:
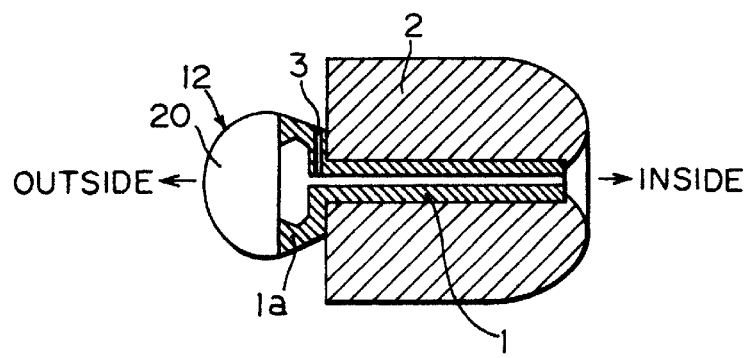
FIG. 1 shows a partial cross-sectional view of the prior art ear plug.

In these drawings, 1,21 . . . core member
2 . . . sleeve member
3,4,6,7,8,9,11 . . . vent or hole
5,10 . . . projection
12 . . . hearing aid
13 . . . external auditory canal
14 . . . lumen
15,25 . . . ear plug
20 . . . sound amplifier portion

EMBODIMENTS OF THE INVENTION

Preffered embodiments of the present invention will be now described with reference to attached drawings.

Figure 2:
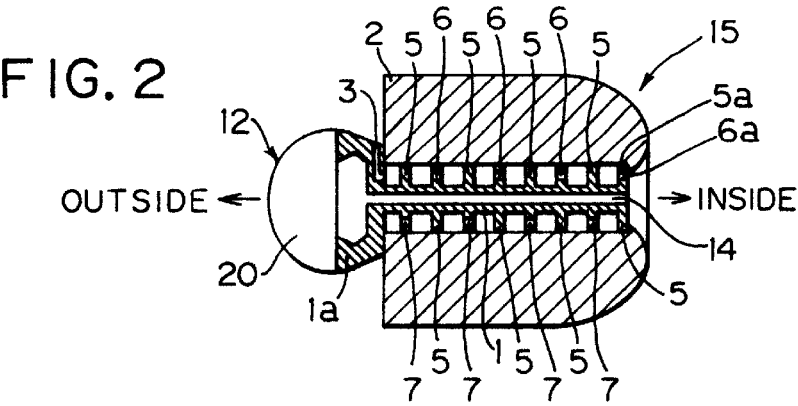
FIG. 2 shows a partial cross-sectional view of an ear plug of a first embodiment of the present invention.
Figure 3:
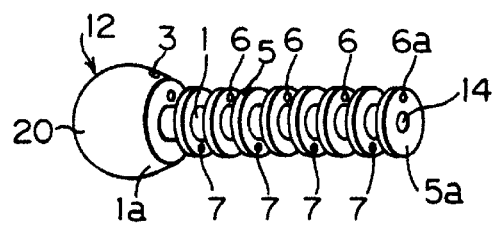
FIG. 3 shows a perspective view of a core member of the ear plug of FIG. 2.

FIG. 2 shows an improved ear plug 15 of the present invention comprising a core member 1 composed of a flexible material such as polyethylene having a penetrating lumen 14 formed inside from one end to another end, plural disc-like or ring-shaped projections 5 or annular flanges formed intermittently on an exterior of the core member 1, and a compressible sleeve member 2 composed of a sponge-like material such as polyurethane. The sleeve member 2 is attached to the core member 1 through an adhesive agent (not shown) adhered particularly between the circumference of the projections 5 and the sleeve member 2 so as to maintain respective spaces between adjacent projections 5.

The projections 5 have vents (for example, notches or holes) 6 and 7 penetrating through each wall portion. Among these vents, an innermost vent 6a is formed through an innermost projection 5a of the projections 5 (or another vent 4 (see FIG. 5) can be formed instead through an inner end portion of the core member 1) to open into the external auditory canal, other vents 5 are formed through other respective projection 5, and an outermost vent 3 is formed as a penetrating hole through an enlarged outer end portion 1a of the core member 1 to open into the external atmosphere. The vents 6 and 7 are formed at different positions (or at an angular interval of 180°) of adjacent projections 5 and the vent 7 at the left end communicates with the outermost vent 3.

Figure 4:
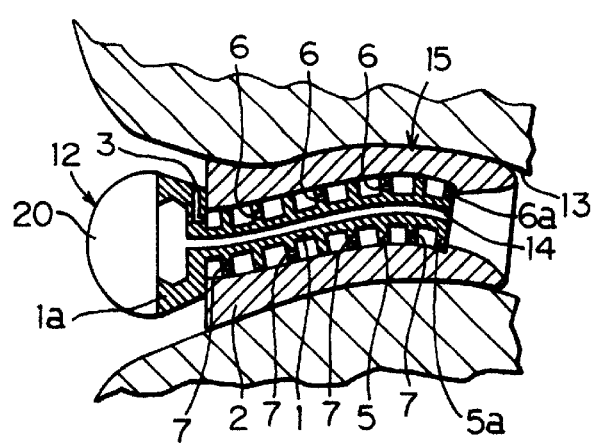
FIG. 4 shows a partial cross-sectional view of the ear plug with a hearing aid when inerted into the external auditory canal.

When the ear plug 15 with a hearing aid 12 in one body is inserted into the external auditory canal 13 as shown in FIG. 4, the sleeve member 2 composed of a sponge-like material is elastically compressed by an inner wall surface of the external auditory canal 13 while the core member 1 is flexibly deformed so as to meet the shape of the external auditory canal 13.

According to this construction of the ear plug 15, the projections 5 are formed on the exterior of the core member 1 as well as the vents 6 and 7 are defined through the projections 5 to make the external auditory canal 13 communicate with the external atmosphere, so as to lengthen a communicating passage or vent to an effective degree for remarkably decreasing only the pressure difference between an inside of the external auditory canal 13 and the external atmosphere as well as preventing leakage of sound causing so-called howling. Because succeeding vents 6 and 7 are deployed differently on each projection, the path of the vent is serpentine.

Figure 5:
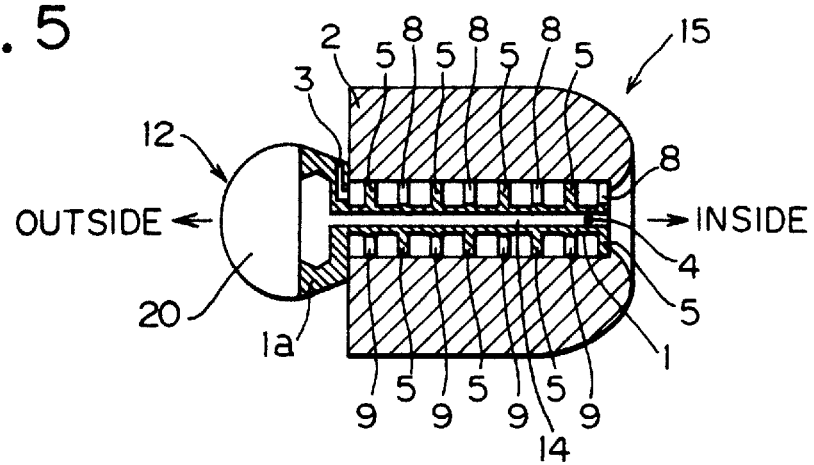
FIG. 5 shows a partial cross-sectional view of an ear plug of a second embodiment of the present invention.
Figure 6:
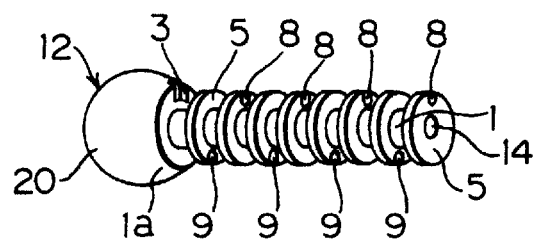
FIG. 6 shows a perspective view of a core member of the ear plug of FIG. 5.

The positions of the vents 6 and 7 serve to effectively lengthen the communicating passage. These vents can be formed as notched portions 8 and 9 at different positions of respective projections 5, particularly at-an angular interval of 180° according to a second embodiment of the present invention as shown in FIGS. 5 and 6. The outermost vent 3 can be easily formed when it is groove-shaped instead of the penetrating hole of FIG. 2.

Figure 7:
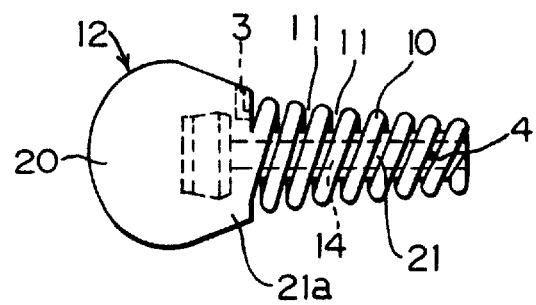
FIG. 7 shows a front view of a core member of an ear plug of a third embodiment of the present invention.

FIG. 7 shows a third embodiment of a core member of an ear plug wherein a continuous vent or groove 11 is formed along a continuously formed spiral-shaped projection or ridge 10 like a single projection to make the outermost vent 3 communicate with the external auditory canal.

Also in this construction of the ear plug of FIG. 7 having the core member 21 with the spiral-shaped projection 10 and the sleeve member 2 as already shown in FIG. 2, the continuous vent 11 extending along the projection 10 serves to make the external auditory canal 13 communicate with the external atmosphere so as to lengthen a communicating passage or vent to an effective degree for remarkably decreasing only the pressure difference between the inside of the external auditory canal 13 and the external atmosphere as well as preventing leakage of sound causing so-called howling. Besides, the spiral-shaped projection 10 can be easily formed on the core member 21 like an external thread.

Figure 8:
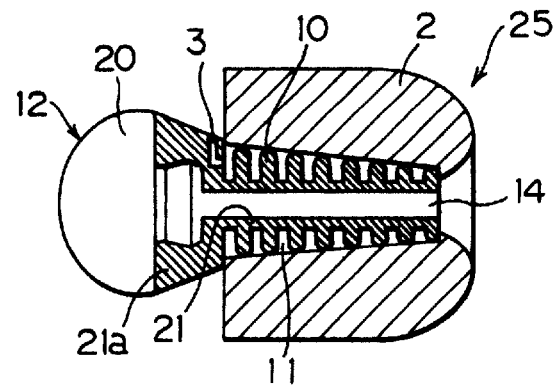
FIG. 8 shows a partial cross-sectional view of an ear plug with a hearing aid.

FIG. 8 shows a further embodiment 25 of an ear plug with a hearing aid 12 having the sleeve member 2 attached to the core member 21 as shown in FIG. 7.

The above-described ear plug 15 or 25 comprises the hearing aid 12 having a sound amplifier portion 20 and a sound guide portion 1 or 21 which functions also as a core member, the plural projections 5 or the spiral-shaped projection 10 formed on the exterior of the sound guide portion 1 or 21 wherein the vent 6 or 11 is defined in respective projections 5 or 10 and the outermost vent 3 is defined in the enlarged portion 1a or 21a of the core member, and the compressible sleeve member 2 adhered to the circumference of the projection 5 or 10.

The ear plug 25 can be easily manufactured as well as the ear plug 15 because the core member is a part of the hearing aid 12 and so it is not necessary to attach a separate hearing aid to the core member. Moreover, the afore said embodiments shown in FIG. 2 to FIG. 7 can be variously modified, for example, a separate hearing aid can be attached to the outer end portion 1a or 21a of the core member 1 or 21. If only ear plug is required, the hearing aid 12 should be omitted in which the penetrating lumen 14 can be closed or can not be formed.

What is claimed is:

1. In an ear plug to be inserted into the external auditory canal, the ear plug comprising a compressible sleeve member including an inner core space when the sleeve member is in an un-compressed state, and a core member insertable into the inner core space to make contact with the sleeve member;

the improvement in which the core member comprises a series of projections disposed longitudinally along an exterior of said core member, such that the sleeve member is supported by contact of the sleeve member on the projections of the core member, and the projections comprise a vent to make the external auditory canal, on an interior of said ear plug, communicate with the external atmosphere through said ear plug when said ear plug is inserted into the external auditory canal.

2. The ear plug as stated in claim 1, wherein a continuous vent or groove is formed along said series of projections to make an outermost end of said vent communicate with the external auditory canal, and said outermost end of said vent is formed through an outer end portion of said core member to open into the external atmosphere.

3. The ear plug as stated in claim 1, wherein said sleeve member is comprises a spongiform material and said core member is flexible so as to be deformed to meet the shape of said external auditory canal.

4. The ear plug as stated in claim 1, wherein a penetrating lumen is formed through an inside of said core member from one end to another end.

5. The ear plug as stated in claim 4, wherein a hearing aid has said core member in one body.

6. The ear plug as stated in claim 1, wherein the series of projections comprises a spiral ridge along the exterior of said core member.

7. The ear plug as stated in claim 1, wherein the series of projections comprises a series of annular flanges along the exterior of said core member.

8. The ear plug as stated in claim 7, wherein said vent comprises a respective hole or notch in each one of the series of annular flanges.

9. The ear plug as stated in claim 8, wherein succeeding holes or notches are deployed differently on each projection, whereby said vent is serpentine.

10. An ear plug to be inserted into the external auditory canal, having a compressible sleeve member and a core member attached therein, the improvement in which plural projections or a single projection are formed intermittently or continuously on an exterior of said core member, and a vent is formed through or along said projection to make said external auditory canal communicate with the external atmosphere when inserted into said external auditory canal, wherein an innermost vent is formed through an innermost projection of said intermittently formed projections or through an inner end portion of said core member to open into said external auditory canal, other vents are formed through other respective projections, and an outermost vent is formed through an outer end portion of said core member to open into the external atmosphere.

11. The ear plug as stated in claim 10, wherein said vents are formed at different positions of adjacent projections.

12. The ear plug as stated in claim 10, wherein each of said projections is ring-shaped.

13. An ear plug to be inserted into the external auditory canal, having a compressible sleeve member and a core member attached therein, the improvement in which plural projections or a single projection are formed intermittently or continuously on an exterior of said core member, and a vent is formed through or along said projection to make said external auditory canal communicate with the external atmosphere when inserted into said external auditory canal, wherein a continuous vent or groove is formed along said continuously formed projection to make an outermost vent communicate with said external auditory canal, and said outermost vent is formed through an outer end portion of said core member to open into the external atmosphere, and wherein an additional vent is formed through an inner end portion of said core member.

14. An ear plug to be inserted into the external auditory canal, having a compressible sleeve member and a core member attached therein, the improvement in which plural projections or a single projection are formed intermittently or continuously on an exterior of said core member, and a vent is formed through or along said projection to make said external auditory canal communicate with the external atmosphere when inserted into said external auditory canal, wherein a continuous vent or groove is formed along said continuously formed projection to make an outermost vent communicate with said external auditory canal, and said outermost vent is formed through an outer end portion of said core member to open into the external atmosphere, and wherein said continuously formed projection is spiral-shaped.

* * * * *